(12) United States Patent
Marks et al.

(10) Patent No.: US 11,925,569 B1
(45) Date of Patent: Mar. 12, 2024

(54) POROUS PROSTHETIC SLEEVE LINER MATERIAL

(71) Applicant: Arrowhead Center, Inc., Las Cruces, NM (US)

(72) Inventors: Robyn Marks, Waterford, MI (US); Reza Foudazi, Las Cruces, NM (US); Neda Sanatkaran, Ames, IA (US); Ryan Zowada, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 1110 days.

(21) Appl. No.: 16/666,192

(22) Filed: Oct. 28, 2019

Related U.S. Application Data

(60) Provisional application No. 62/751,306, filed on Oct. 26, 2018.

(51) Int. Cl.
*A61F 2/78* (2006.01)
*A61F 2/30* (2006.01)
(Continued)

(52) U.S. Cl.
CPC .......... *A61F 2/7812* (2013.01); *B29C 39/003* (2013.01); *B29C 39/026* (2013.01); *B29C 44/3403* (2013.01); *B29C 44/56* (2013.01); *C08F 2/32* (2013.01); *A61F 2002/30024* (2013.01); *A61F 2002/7818* (2013.01); *A61F 2002/7837* (2013.01); *B29K 2033/04* (2013.01); *B29K 2033/26* (2013.01)

(58) Field of Classification Search
CPC ..................................................... A61F 2/7812
See application file for complete search history.

(56) References Cited

U.S. PATENT DOCUMENTS 5,258,037 A 11/1993 Caspers
5,376,129 A 12/1994 Faulkner et al.
(Continued)

FOREIGN PATENT DOCUMENTS

CA 2288935 A1 11/1998
CA 2402715 C 1/2010
(Continued)

OTHER PUBLICATIONS

Wu, Ranting, Angelika Menner, and Alexander Bismarck. "Tough Interconnected Polymerized Medium and High Internal Phase Emulsions Reinforced by Silica Particles." Journal of polymer science. Part A, Polymer chemistry 48.9 (2010): 1979-1989. Web. (Year: 2010).*

(Continued)

*Primary Examiner* — Seyed Masoud Malekzadeh
*Assistant Examiner* — Timothy G Hemingway
(74) *Attorney, Agent, or Firm* — Justin R. Jackson; Peacock Law P.C.

(57) ABSTRACT

A material that can be formed into a porous prosthetic sleeve liner that provides particularly useful benefits for prosthetics. The material is breathable and sweat-absorbing, thus minimizing skin morbidity when used as a prosthetic liner. The material can include hydrophilic-lined continuous pores within a hydrophobic polymer, wherein the hydrophilic lining is crosslinked together with the hydrophobic polymer via non-degradable covalent interactions using chain crosslinkers.

18 Claims, 5 Drawing Sheets

(51) Int. Cl.
*B29C 39/00* (2006.01)
*B29C 39/02* (2006.01)
*B29C 44/34* (2006.01)
*B29C 44/56* (2006.01)
*B29K 33/00* (2006.01)
*B29K 33/04* (2006.01)
*C08F 2/32* (2006.01)

(56) References Cited

U.S. PATENT DOCUMENTS

| | | |
|---|---|---|
| 5,534,034 A | 7/1996 | Caspers |
| 6,136,039 A | 10/2000 | Kristinsson et al. |
| 6,440,345 B1 | 8/2002 | Hellberg |
| 6,626,952 B2 | 9/2003 | Janusson et al. |
| 7,001,563 B2 | 2/2006 | Janusson et al. |
| 8,535,389 B2 | 9/2013 | McKinney |
| 9,066,820 B2 | 6/2015 | MacKenzie |
| 9,574,058 B2 * | 2/2017 | Foudazi .............. C08J 9/28 |
| 2003/0113494 A1 | 6/2003 | Janusson et al. |
| 2007/0055383 A1 | 3/2007 | King |
| 2008/0188949 A1 | 8/2008 | MacKenzie |
| 2012/0041568 A1 | 2/2012 | MacKenzie |
| 2015/0079014 A1 | 3/2015 | Ingvarsson et al. |
| 2016/0030207 A1 | 2/2016 | Walters et al. |
| 2018/0049897 A1 | 2/2018 | Lathers et al. |

FOREIGN PATENT DOCUMENTS

| | | |
|---|---|---|
| CN | 108890861 A | 11/2018 |
| EP | 1322267 B1 | 3/2011 |
| EP | 1588244 B1 | 9/2016 |
| JP | 2013043032 A | 3/2013 |
| WO | 0167842 A1 | 9/2001 |
| WO | WO-2009067087 A1 * | 5/2009 ......... B01D 67/0093 |

OTHER PUBLICATIONS

Wu, Ranting, Angelika Menner, and Alexander Bismarck. "Macroporous Polymers Made from Medium Internal Phase Emulsion Templates: Effect of Emulsion Formulation on the Pore Structure of polyMIPEs." Polymer (Guilford) 54.21 (2013): 5511-5517. Web. (Year: 2013).*

Anthes, Emily, "A Dolphin's Tale", Scientific American, vol. 308, No. 3, 2013, 78-81.

Porticos, "Porticos Makes Advancements in Amputee Heat Issues", http://www.porticos.net/porticos-makes-advancements-in-amputee-heat-issues, Feb. 20, 2013.

Stone, K. R., et al., "Meniscal regeneration with copolymeric collagen scaffolds: In vitro and in vivo studies evaluated clinically, histologically, and biochemically", Am J Sports Med., vol. 20, No. 2 (Abstract only), 1992.

* cited by examiner

Hydrophillic, Porous polyHIPE Foam

|  | WVT (g/m²*h) |
|---|---|
| Present Invention | 56.9 |
| Commercial Liner | 8.6 |
| Open Environment | 117.9 |

POROUS PROSTHETIC SLEEVE LINER MATERIAL

CROSS-REFERENCE TO RELATED APPLICATIONS

This application claims priority to and the benefit of the filing of U.S. Provisional Patent Application No. 62/751,306, entitled "Prosthetic Sleeve Liners", filed on Oct. 26, 2018, and the specification thereof is incorporated herein by reference.

STATEMENT REGARDING FEDERALLY SPONSORED RESEARCH OR DEVELOPMENT

Not Applicable.

BACKGROUND OF THE INVENTION

Field of the Invention (Technical Field)

Embodiments of the present invention relate to prosthetics. More particularly, embodiments of the present invention provide a solution for prosthetic liner systems, most preferably using a crosslinked copolymeric system with interconnected porous structure obtained from templating of emulsion with adjustable volume fraction.

DESCRIPTION OF RELATED ART

Currently, prosthetic liners are made of hydrophobic, nonporous silicone or polyurethane as a base material. As skin morbidity is a highly recognized concern with prosthetic sleeves, many current commercially available liners have alterations to these base materials to encourage skin health. These improvements, as well as others still in research phases, include, but are not limited to medicated coatings, cooling systems, and vacuum attachments. However, instead of correcting the root of the problem, i.e. the inadequate material properties, they aim to treat the secondary problems caused by those materials: heat and sweat buildup, pistoning, and microbial growth. Most of these liner improvements function in a retrograde manner, treating the problem after it has arisen. Therefore, there is a need for liners that prevent skin wear from the start rather than those that will only treat breakdown or infection once it has already developed.

Silicone and polyurethane have been used for decades in liners due to their high mechanical strength. Some of these liners can be selected to correlate with the needs of the patient depending on their degree of athletic participation and skin strength. If the liner's structure undergoes creep induced deformation, or the limb shape changes overtime, the connection between liner and peripheral limb loosen up. As a result, the patient experiences uncoupled longitudinal motion between the liner and the rigid external prosthesis in a phenomenon known as pistoning. Sweat buildup adds to the pistoning by allowing extra motion along the limb-liner interface. The unwanted motion causes skin wear, which ultimately allows a route of infection for microbes whose survival is reinforced by the warm, moist environment created by a poorly ventilated limb-liner interface.

The sweat buildup is one of the major causes of skin irritations within prosthetic sleeve liners. The liners are intended to be placed over the limb stump in order to reduce pressure and friction from the rigid prosthetic limb. However, due to the hydrophobic nature of the current materials for the liners, silicone and polyurethane, sweat is unable to escape the limb-liner interface. This sweat buildup leads to increased motion within the sleeve and commonly leads to a variety of skin irritations. The wear on the skin causes an inflammatory response leading to further complications such as ulcers and extensive tissue necrosis. Due to the large quantity of normal bacterial flora on the skin surface, such as the Staphylococci and *Corynebacterium* genus, opportunistic infections are easily propagated once a route through skin layers is provided. In this case, skin wear causes breakdown, often around hair follicles, and continues to progress deeper towards the subdermal blood supply through which the infectious organisms can readily be spread. Additionally, fungal infections, such as tinea corporis, can lead to nonspecific scaling and erythemous eruptions on the skin surface. These multiple sources of infection illustrate the threat of sweat buildup as it leads to a snowball effect of disease processes which cause further morbidity to the amputee population. This is an especially critical concern for patients with decreased wound healing capability, including those suffering from diabetes and peripheral vascular disease as well as patients living in a humid subtropical climate. Reports show that these vascular diseases can make up an estimated 54% of lower limb amputations. There is thus a present need for a breathable, sweat-absorber sleeve with minimal skin morbidity.

BRIEF SUMMARY OF THE INVENTION

Embodiments of the present invention relate to a method for forming a material including forming a hydrophobic polymer, forming interconnected pore spaces within a continuous phase of the hydrophobic polymer, employing internal phase emulsion templating—the internal phase emulsion templating selected from medium internal phase emulsion ("MIPE") templating and/or high internal phase emulsion ("HIPE") templating, forming a hydrophilic pore lining from hydrophilic chemical end groups of a second polymer lined within the interconnected pore spaces of the hydrophobic polymer, the hydrophilic chemical end groups formed from a hydrophilic monomer polymerized selectively at a surface of the hydrophobic polymer, and crosslinking together the continuous phase of the hydrophobic polymer to the hydrophilic pore lining via covalent interaction using a chain crosslinker.

The hydrophobic monomers, the chain crosslinker, and an additive can be used in the continuous phase. In one embodiment, the internal phase emulsion templating can be stabilized with one or more surfactants. An aqueous phase containing a hydrophilic monomer can be dispersed into the continuous phase prior to polymerization of the hydrophobic polymer. The aqueous phase containing a hydrophilic monomer can be dispersed into the continuous phase by dropwise addition, by injection, and/or by pouring. The hydrophilic monomer preferably copolymerizes with the hydrophobic monomer at an aqueous-oil interface. The method can further include passing a mixture of the continuous phase and the aqueous phase through a barrier with a plurality of openings and/or through a static blade to cause it to break up.

In one embodiment, connection of the interconnected pores preferably occurs during the polymerization reaction and the voids of the interconnected pores are subsequently emptied following removal of components that are unreacted or unreactive. Optionally, employing internal phase emulsion templating can include employing a hydrophilic, porous polyHIPE foam. The hydrophilic, porous polyHIPE foam can include a foam with interconnected hydrophilic pores with a hydrophobic core.

Optionally, employing internal phase emulsion templating can include employing a hydrophilic, porous polyMIPE foam. The hydrophilic, porous polyMIPE foam can include a foam with interconnected hydrophilic pores with a hydrophobic core. In one embodiment, forming interconnected pore spaces can include forming interconnected pore spaces by templating the emulsion with an adjustable volume fraction. The method can include forming hydrophilic chemical end groups from one or more of 2-hydroxyethyl acrylate, 2-hydroxyethyl methacrylate, sodium acrylate, 2-hydroxyethyl acrylate, poly(propylene fumarate), poly(propylene glycol)-acrylates and diacrylates, poly(propylene glycol)-methacrylates and dimethacrylates, poly(ethylene glycol)-acrylates and diacrylates, poly(ethylene glycol)-methacrylates and dimethacrylates, acrylic acid, N-isopropyl acrylamide, acrylamide, acrylonitrile, glacial methacrylic acid, 2-(acryloyloxy)ethyl-trimethylammonium chloride, [2-(methacryloyloxy)ethyl]trimethyl ammonium, N,N'Methylene(bis)acrylamide, N,N-diethylacrylamide, N,N-Diethylaminoethyl methacrylate, N,N-Diethylaminoethyl methacrylate, and 2-acrylamido-2-methyl-1-propanesulfonic acid, and/or a combination thereof.

The method can include altering mechanical and structural properties of the material by varying a monomer to crosslinker ratio, varying mixing and addition methods of a dispersed phase, varying polymerization and casting methods, and/or varying a ratio of continuous phase to dispersed phase. Optionally, the method can include pouring an emulsion into a gap formed between a mold and a cast and allowing it to cure therein. The method can also include forming the material into a prosthetic liner and/or into a sleeve. The method can further include providing an additive to the continuous phase of the hydrophobic polymer prior to dispersal of the hydrophilic monomer to increase elasticity and/or strength of the material. Optionally, providing the additive can include providing a material selected from silica micro-particles, silica nano-particles, clay particles, carbon nanotubes, nanocellulose, high molecular weight polymers, and/or combinations thereof. Optionally, cross-linking together the continuous phase of the hydrophobic polymer to the hydrophilic pore lining via covalent interaction using a chain crosslinker can include a non-degradable covalent interaction.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

An embodiment of the present invention relates to improving the design of prosthetic systems by focusing on a patient centered prosthetic system. Specifically, an embodiment of the present invention comprises a design of a material to be used within current prosthetic liner systems. This material includes a unique copolymer of hydrophobic and hydrophilic constituents that can combine favorable properties of multiple compounds to form a single material. According to an embodiment of the present invention, the single material synthesized maintains functional mechanics in the weight bearing application while preventing amputee skin morbidity.

Figure 1:
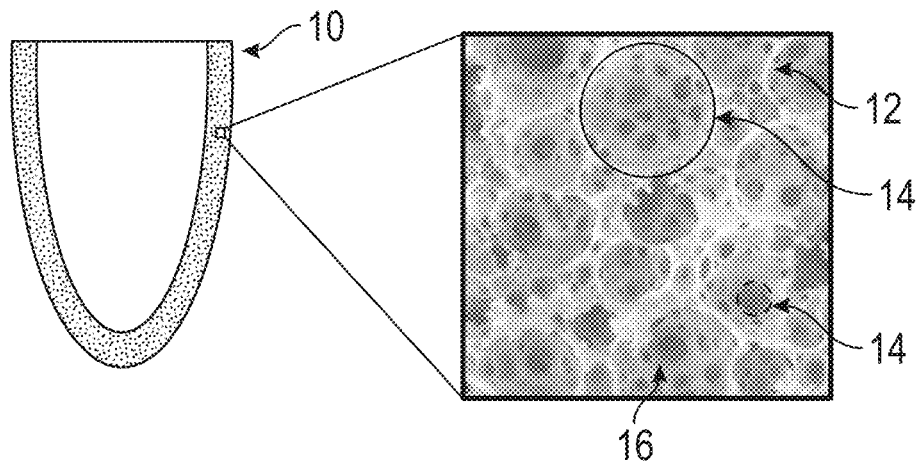
FIG. 1 illustrates a general structure of a porous liner of the present invention.

Referring to FIG. 1, the structures of the present invention illustrated are magnified as the trued porous structure on the micron and sub-micron scales. The overall structure of liner 10 is an exemplary continuous phase 12 of a preferably hydrophobic polymer that has mechanically robust properties and that maintains its strength throughout cyclic compression of the gait cycle. Monomers are preferably polymerized to produce a hydrophobic phase, including, but are not limited to: (MA) methylacrylate, (BA) butyl acrylate, (EHA) 2-ethylhexyl acrylate, (EA) ethyl acrylate, (BMA) butyl methacrylate, (EMA) ethyl methacrylate, (TMPTA) trimethylolpropane triacrylate, (MMA) methyl methacylate, (GMA) glycidyl methacrylate, (t-BA) t-butyl acrylate, (HBMA) hydroxybutyl methacrylate, (S) styrene, siloxanes, (CL) caprolactone, (U) urethanes, (IP) isoprene, and (VP) vinylpyridine. When polymerized, the mechanical properties of these monomers preferably fit within the mechanical criteria required for a liner. Within the continuous phase, there are preferably interconnected pore spaces 14 that are preferably lined with hydrophilic chemical end groups 16 of a second polymer. The hydrophilic monomers used can include, but are not limited to: (HEA) 2-hydroxyethyl acrylate, (HEMA) 2-hydroxyethyl methacrylate, (SA) sodium acrylate, (HEA) 2-hydroxyethyl acrylate, (PPF) poly(propylene fumarate), (PPG-A) poly(propylene glycol)-acrylates and diacrylates, (PPG-MA) poly(propylene glycol)-methacrylates and dimethacrylates, (PEG-A) poly(ethylene glycol)-acrylates and diacrylates, (PEG-MA) poly(ethylene glycol)-methacrylates and dimethacrylates, (AA) acrylic acid, (NIPAM) N-isopropyl acrylamide, (AAm) acrylamide, (AN) acrylonitrile, (GMAA) glacial methacrylic acid, (AOETMA) 2-(acryloyloxy)ethyl-trimethylammonium chloride, (MAOETMA) [2-(methacryloyloxy)ethyl]trimethyl ammonium, (MBAA) N,N'Methylene(bis)acrylamide, (DEAA) N,N-diethylacrylamide, (DEAEA) N,N-Diethylaminoethyl methacrylate, (DEAEMA) N,N-Diethylaminoethyl methacrylate, and (AMPS) 2-acrylamido-2-methyl-1-propanesulfonic acid. These monomers have been chosen due to their hydrophilic nature and ability to be polymerized selectively at the surface of the hydrophobic polymer. The hydrophobic continuous phase and hydrophilic pore lining are preferably crosslinked together via non-degradable covalent interactions using chain crosslinkers 18. The crosslinking process adds to the mechanical robustness of the system while the backbone of the crosslinking molecule allows increased elasticity of the overall material system. The crosslinking molecules used can include, but are not limited to: (PEGDA) polyethylene glycol diacrylate, (PEGDMA) polyethylene glycol dimethacrylate, (EGDA) ethylene glycol diacrylate, (DEGDA) diethylene glycol diacrylate, (TEGDA) triethylene glycol diacrylate, (t-EGDA) t-ethylene glycol diacrylate, (HEGDA) hexaethylene glycol diacrylate, (EGDMA) ethylene glycol dimethacrylate, (DEGDMA) diethylene glycol dimethacrylate, (TEGDMA) triethylene glycol dimethacrylate, (t-EGDMA) tetraethylene glycol dimethacrylate, (HEGDMA) hexaethylene glycol dimethacrylate, (MDMA) Methylene dimethacrylate, (TMPTA) Trimethylolpropane triacrylate, (TMPTMA) trimethylolpropane trimethacrylate, (DVB) Divinylbenzene, (BDMA) N,N'-butanediol dimethacrylate, (GelMA) gelatin methacrylate, and (PFDMA) propylene fumarate dimethacrylate. These various crosslinking molecules preferably expand the mechanical properties of the liner material. Each crosslinking molecule will provide a specific mechanical strength and durability to custom fit the patient's needs.

To increase the mechanical properties of the bulk phase of the material, additives are preferably added to the hydrophobic phase of the liner that can increase the elastic moduli and strength of the material depending on the additive properties. These additives can include, but are not limited to: silica micro- and nano-particles, clay particles, carbon nanotubes, nanocellulose, and high molecular weight polymers comprised of the monomers listed in the immediately preceding paragraph. These materials can be introduced to the continuous phase prior to or after the hydrophilic monomer is dispersed into the oil phase as discussed in the following paragraph.

Figure 2:
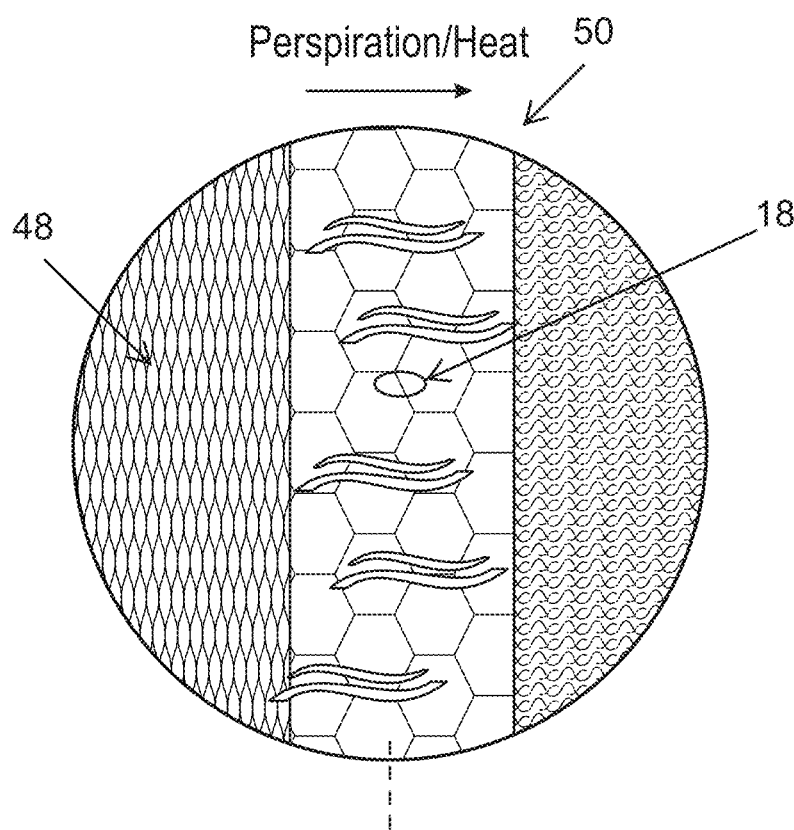
FIG. 2 is a schematic of the structure of the porous liner of the present invention.

As illustrated in FIG. 2, embodiments of the present invention combine multiple materials with favorable properties into single crosslinked copolymer system 50 preferably through emulsion (medium internal phase emulsion ("MIPE") and/or high internal phase emulsion ("HIPE")) templating, during which robustness can be retained while simultaneously introducing interconnected hydrophilic pore spaces. In one embodiment, MIPE is said to exist when less than about 74% volume is aqueous phase, whereas HIPE is said to exist when greater than about 74% value is aqueous phase. This 'water-in-oil' emulsification method of synthesis uses hydrophobic monomers, crosslinkers, and additives as the oil phase, which will ultimately form the bulk of the final material scaffold. The emulsions are preferably stabilized with proper surfactants, examples of which are listed later in this application. Before polymerization, an aqueous phase containing a hydrophilic monomer is dispersed into the oil phase, either by drop-wise addition, by injection, or by pouring depending on the method of mixing and scale of production. Upon curing, the hydrophilic monomer is copolymerized with the hydrophobic monomer at the aqueous-oil interface. The interconnection of pores occurs in two steps. First, connection is achieved during the polymerization reaction. Second, the voids are emptied, most preferably fully emptied, following the removal of unreacted/unreactive components. Ultimately, the mechanically robust hydrophobic polymer forms the bulk continuous phase and the hydrophilic polymer coats the porous surface, thus, retaining the ability to wick sweat away from the residual limb surface 48. This material synthesis technique additionally allows individualized design for each patient, taking into account both shape and internal material properties.

In another embodiment of the present invention, single crosslinked copolymer system 50 is a hydrophilic, porous polyMIPE and/or polyHIPE foam. In another embodiment of the present invention, the hydrophilic, porous polyMIPE and/or polyHIPE foam can have interconnected hydrophilic pores, with a hydrophobic core. Hydrophilicity and porosity wicks sweat and heat away from the limb interface. A hydrophobic core provides mechanical stability and resilience.

Figure 3:
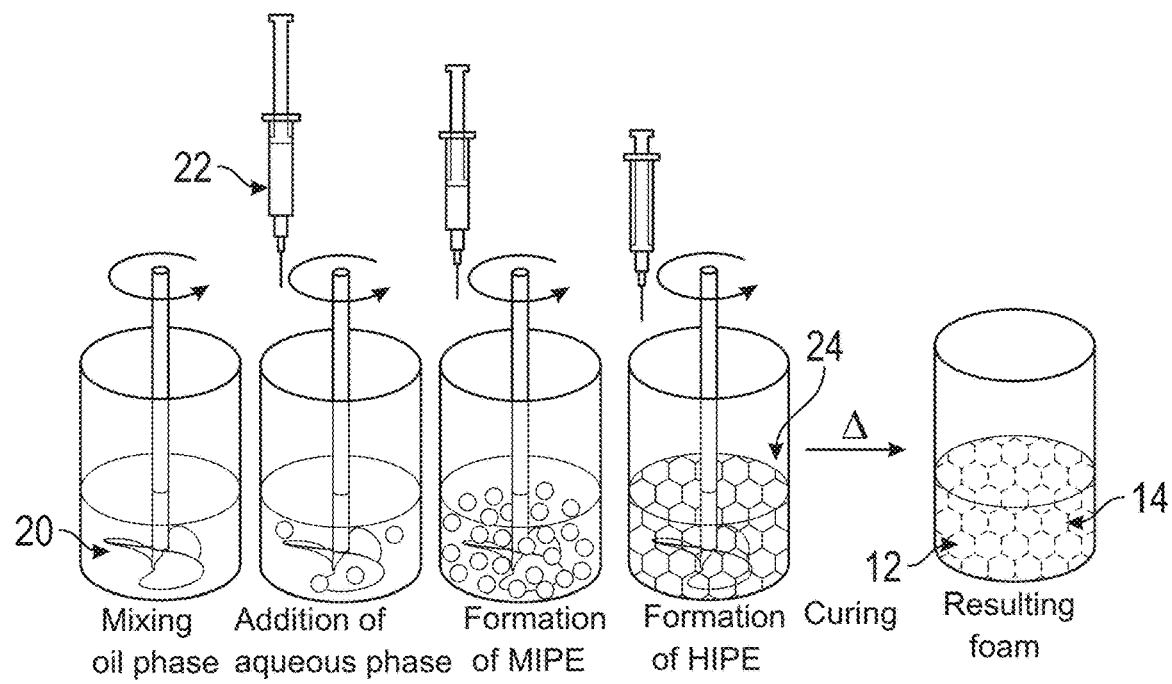
FIG. 3 illustrates a basic synthesis process of the liners of the present invention from forming an emulsion to the curing process during which the materials polymerize and crosslink.

The material according to an embodiment of the present invention can be synthesized via a water-in-oil emulsion process, as illustrated in FIG. 3. Oil phase (also occasionally referred to herein as the "continuous phase") 20 preferably comprises the hydrophobic material. Aqueous phase (also occasionally referred to herein as the "dispersed phase") 22, preferably comprises the hydrophilic material, is added to the oil phase where it is broken into droplets. The droplet break-up can be achieved by, but is not limited to: mechanical mixing, sonication, homogenizer and/or static mixing. Droplet breakup occurs when external forces overcome the interfacial forces of droplets. The suspended droplets, which form emulsion 24, are preferably stabilized using surfactants and stabilizers to retain their morphology. Surfactants which can be used include but are not limited to polyglycerol polyricinoleate (PGPR), block copolymers of polyethylene and polyethylene glycol, block copolymers of polyethylene glycol and propylene glycol, diacrylated block copolymers of polyethylene glycol and polyethylene glycol, sorbitan-based surfactants, and polyhedral oligomeric silsesquioxane molecules. The surfactants preferably form water-in-oil emulsions. Stabilizers can include but are not limited to: sodium chloride, potassium chloride, calcium chloride, magnesium chloride, sodium sulfate, potassium sulfate, calcium sulfate, magnesium sulfate, and poly(vinyl alcohol). The stabilizers can be water or oil soluble components. After the dispersed phase has been entirely added to the emulsion 24, it can be cured around the desired shape of the liner. The curing process crosslinks the combination of materials into the continuous phase by using either electromagnetic (ultraviolet, light, etc.), thermal, or reduction-oxidation induced initiation. The materials used as thermal, redox, and/or electromagnetic initiators can include, but are not limited to, potassium persulfate (KPS), ammonia persulfate (APS), sodium persulfate (SPS), azobisisobutyronitrile (AIBN), sulfoxilate (SFS), 1-hydroxycyclohexyl phenyl ketone (HPK), hydroxyacetophenone (HAP), diphenyl(2,4,6-trimethylbenzoyl)phosphine oxide (TPO), 4,4'-azobis(4-cyanovaleric acid), benzophenone (BP), tetramethyl ethylene diameine (TMEDA), benzoyl peroxide (BPO), and 2,4,6-Trimethylaniline (TMA) 12. The choice of initiation method is based on the chosen production method and desired resulting properties of the material. These can include for example, but are not limited to thermal, UV, redox. In one embodiment, UV initiation can provide especially desirable results for 3D printing, and thermal initiation can provide particularly desirable results for injection molding. By evaporating the water out of the dispersed phase, the final pore spaces 14 can be obtained, leading to formation of interconnecting porous structure. The final material includes mainly pore spaces 14 formed within the hydrophobic continuous phase. The surface of the pores is preferably lined with hydrophilic polymer. A web-like interconnection of the pores within the continuous phase makes it an open-cell foam material.

The mechanical and structural properties of the material can be altered by a variation in components and their ratios (e.g. monomer to crosslinking agent ratio), a variation of mixing and addition methods of the dispersed phase, and/or a variation in polymerization and casting methods. By varying the ratio of continuous phase to dispersed phase, the density of the material will change, as the higher the amount of continuous phase the higher the density. Each of these types of variations are independent of one another, e.g. the mechanical and structural properties are dependent on the mixing speed and method, but can still be altered by the component types and ratios. By altering the monomer or crosslinking agent, the prosthetic sleeve liner will vary in mechanical strength, elasticity, and durability based on the crosslink density and functional groups present in both components. The stability of the emulsion will be based on the type and amount of surfactant and stabilizing agent. The dispersed phase addition will vary depending on added hydrophilic monomer, dispersion method, and mixing method. The dispersed phase can be added either through droplet method (i.e. a dropwise addition of dispersed phase), injection method, where a streamline of the dispersed phase is added directly into the continuous phase, or bulk pouring method. The method of dispersion depends highly on the stability of the emulsion (i.e., high phase-inversion potential requires slow addition of dispersed phase). The mixing method can be varied depending on scale of production and applied shear forces (i.e., higher forces create smaller droplets). For a continuous process, the continuous phase would be pumped through the mixer and the dispersed phase would be injected into the mixer through either a streamline or a dropwise manner. The mixture can pass through a barrier or static blade to cause breakup. The barrier preferably has small openings that would cause the droplets of the continuous phase to contract and expand rapidly, resulting in droplet breakup. For static blades, high flow velocity of the droplets across the blades creates a high shear force to break up the droplets. The droplet size will be controlled by the pressure drop along the mixer, the diameter of the openings within the barriers, and the addition rate of the dispersed phase.

Figure 4:
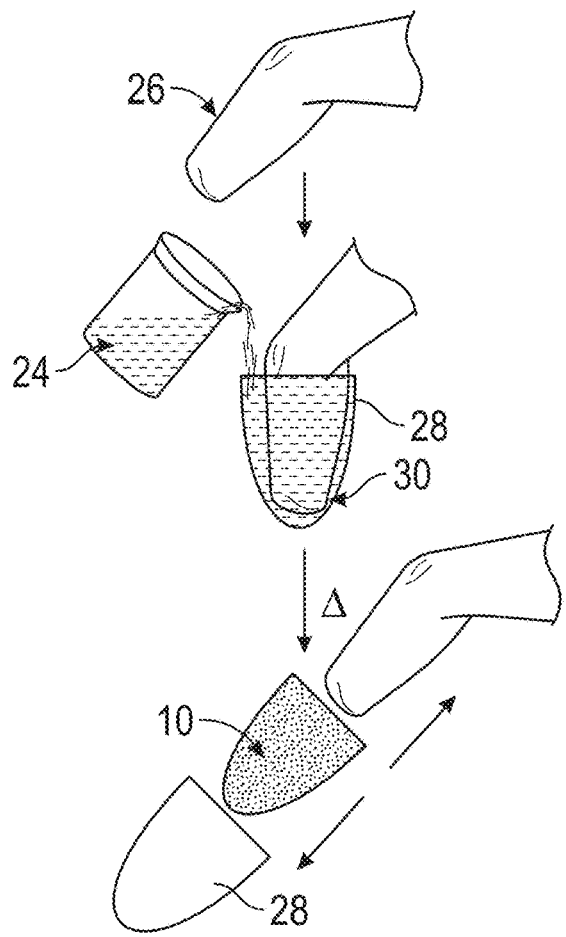
FIG. 4 illustrates an in-situ curing process of the present invention that matches the topography of a patient's residual limb.

Referring to FIG. 4, the in-situ curing technique of the present invention can be altered to accommodate the incorporation into previously developed prosthetic systems. Curing the liner to the precise limb shape can be achieved using two different approaches. In the first approach, as is illustrated in FIG. 4, positive cast 26 of the external surface of an exemplary patient's limb can be developed along with negative mold of rigid prosthetic socket 28 of the patient's prosthesis. The limb cast can be supported within negative mold of prosthetic socket 28 with a gap 30 between 2 mm and 9 mm, depending on the patient's residual limb topography. Before curing, emulsion 24 can be poured into the gap between the mold and cast into the desired liner shape. This method can also be used to cast a standard shaped liner for mass production.

Figure 5:
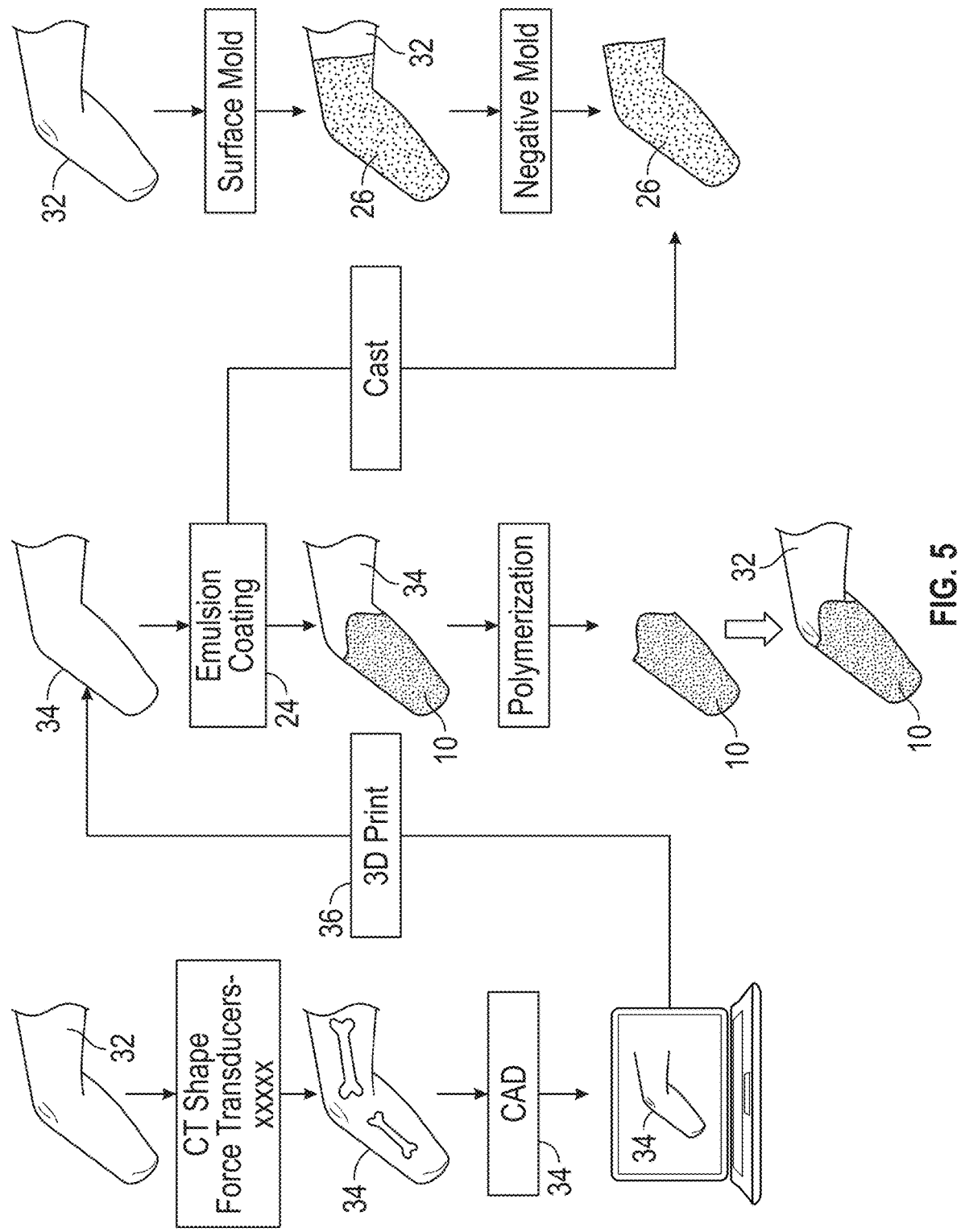
FIG. 5 illustrates in-situ synthesis processes for the porous liner of the present invention.

Referring to FIG. 5, a flowchart of the processes by which embodiments of the present invention can be synthesized is illustrated. In this approach, exemplary patient's limb 32 can be scanned 34 and a customized liner can optionally be manufactured using two techniques: a 3D printer (not shown) can be fed with emulsion 24 and thus can print 36 the liner 10 directly into the exact shape of the scanned limb. Alternatively, as illustrated in FIG. 4, positive cast 26 can be made based on the limb scan. Emulsion 24 can be poured into the mold and cured into the desired liner shape. This method can also be used to cast a standard shaped liner for mass production.

Figure 6:
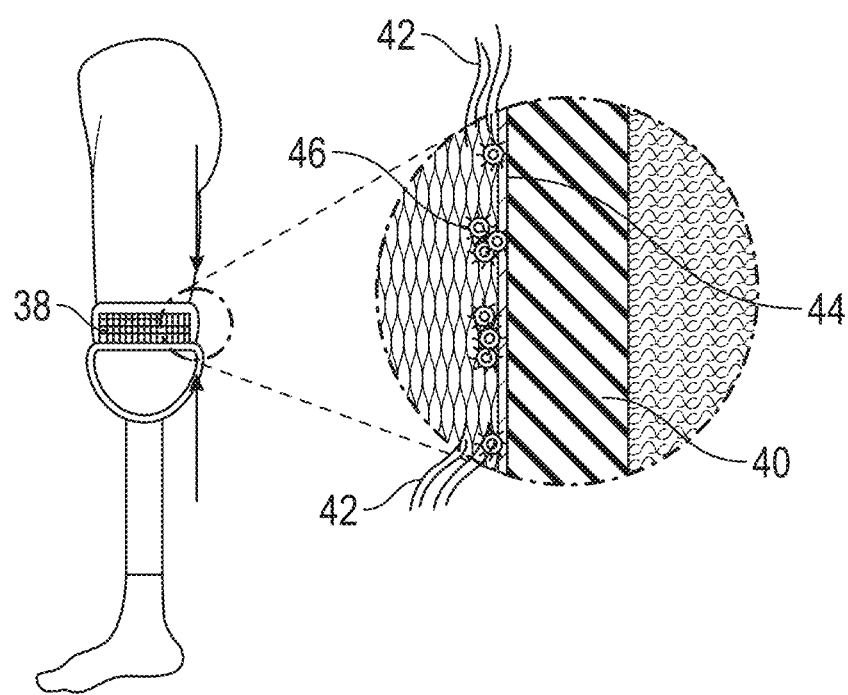
FIG. 6 is a drawing which illustrates bacterial growth that is possible on known liners.

Referring to FIG. 6, prosthetic sleeve liners 38 that are currently and traditionally used cause significant skin morbidity in amputee patients due to the use of suboptimal materials 40. These suboptimal materials 40, e.g., silicone/polyurethane rubber, are hydrophobic and nonporous materials, thus leading to heat and sweat buildup 42 in addition to mechanical creep that enhances longitudinal motion around the limb-liner interface 44. The combination of these unfavorable properties leads to skin wear due to friction around the limb interface and promotion of bacteria and microbial overgrowth 46 around the limb surface. These conditions can additionally lead to skin morbidities including infection and potential need for more proximal amputation.

Figures 7, 8:
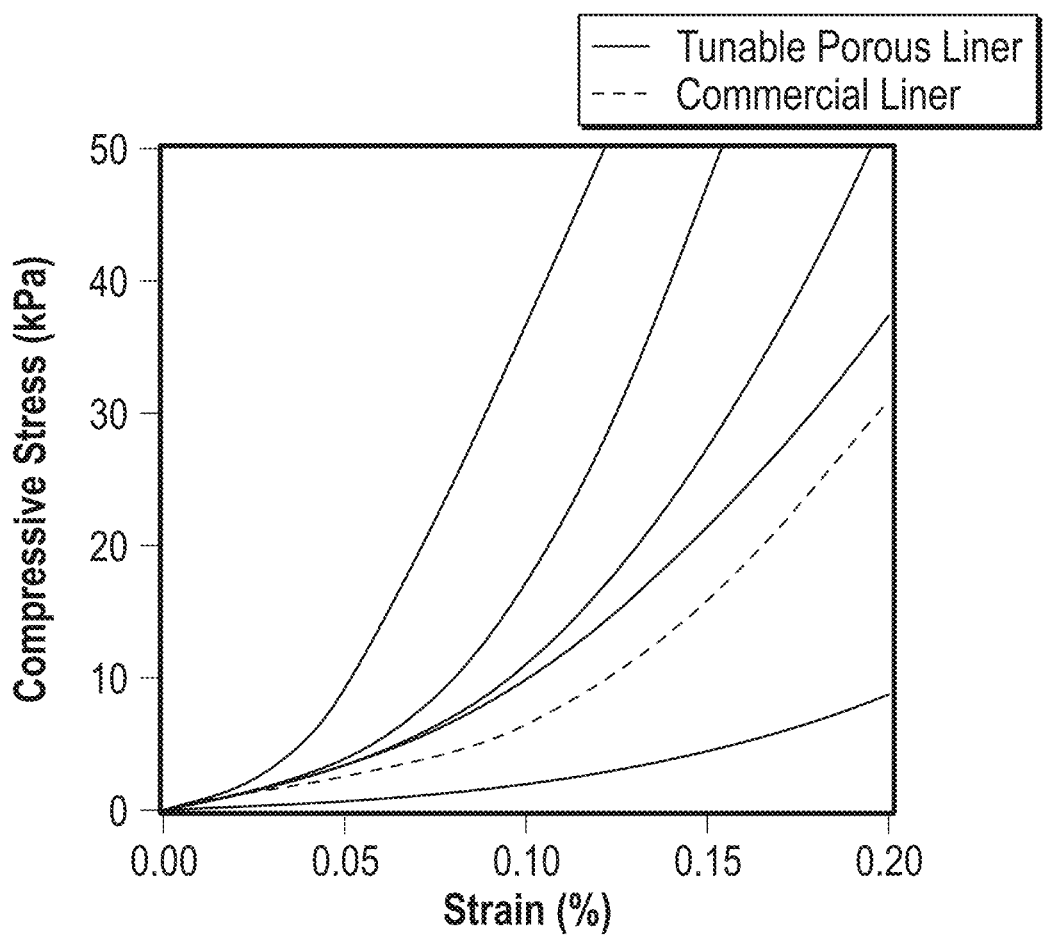
FIG. 7 is a compressive stress-strain chart which illustrates disadvantages of known commercial liners in relation to the numerous tunable liners that are possible in accordance with the teachings of embodiments of the present invention.
FIG. 8 is a table which illustrates the results of a water vapor transmission ("WVT") test wherein a liner constructed according to an embodiment of the present invention was tested as well as a commercially-available liner and the open environment.

According to one embodiment of the present invention, mechanical testing has shown the porous materials have a broad range of mechanical strength depending on the chosen components and porosity. Referring to FIG. 7 the compressive modulus ranges from 50 to 555 kPa within the range of the commercially available liners made of silicone and polyurethane.

Referring to the table of FIG. 8, the results of water vapor transmission ("WVT") tests are illustrated. As can be seen therein, embodiments of the present invention have an average water vapor transmission rate of 57 g/m$^2$ h. This was for a water solution containing 0.5 wt % NaCl as synthetic sweat at 37° C. to simulate human body temperature.

According to an embodiment of the present invention, this material system allows the liner to be tailored to the needs of individual patients. Alteration in the material synthesis technique can alter the balance of mechanical strength with porosity and breathability depending on the patient's mechanical demands, sweat production, and heat generation. Alterations in the curing technique allow individualized sizes and shapes to be developed. The ability to modify the liner without removing the necessary material properties allows this liner material to be incorporated into existing prosthetic systems.

An embodiment of the present invention can decrease patient skin morbidity by providing a material that allows the passage of heat and sweat while remaining mechanically robust.

In one embodiment of the present invention, unique properties achieved in this material system have the potential to increase patient quality of life in many areas including integumentary health, acute and chronic pain, economic burden, and recurrent surgeries. In accordance with the teachings of the present invention, custom liners can optionally be created for each patient considering their residual limb shape and needs relating to sweat wicking, breathability, and biomechanics. Further, patient quality of life can be improved by decreasing skin morbidity as well as pain, financial burden, social limitations, and subsequent surgeries. Embodiments of the present invention can provide a breathable interface between the patient and the prosthetic limb. Sweat wicking interconnected pore spaces can be provided. Optionally, customizable material synthesis methods can be used to fit individual patients. Further, prevention of pistoning using a liner according to an embodiment of the present invention leads to prolonged durability.

With the emulsion templating technique, foam structures with different porosity, pore size, and permeability can be created which can be exploited for balancing the mechanical needs of the suspension system of the sleeve while allowing perspiration and heat flow away from the limb. This approach also allows the shape of each liner to be personalized to best meet the needs of individual patients by coating the peripheral limb and in-situ polymerization of emulsion. An individualized approach to the fit of the prosthetic liner aids in the prevention of further skin irritations by decreasing sweat buildup and friction from movement around the peripheral limb.

Embodiments of the present invention can improve prosthetic sleeve liners by allowing for sweat to be pulled away from the liner-limb interface. The liners according to an embodiment of the present invention are made from polymeric high disperse phase emulsion (polyMIPE and/or polyHIPE) foam through the combination of hydrophobic and hydrophilic monomers. This can be accomplished using an emulsion templating method to create hydrophilic interconnected pores. The hydrophilic pores can allow for breathability of the liner while maintaining mechanical properties needed for the suspension system that allows for the functionality of the prosthetic limb. By reducing sweat buildup at the interface, the potential for bacterial or fungal infections and therefore skin morbidity can be decreased.

INDUSTRIAL APPLICABILITY

The invention is further illustrated by the following non-limiting example.

Example 1

The following is an example of producing a liner using thermal curing according to an embodiment of the present invention:

In one exemplary embodiment, the oil phase of the emulsion is first prepared by mixing ethyl hexyl acrylate ("EHA"), poly(ethylene glycol) diacrylate ("PEGDA"), Pluronic L121 and benzoyl peroxide ("BPO") (the monomer, crosslinker, surfactant and initiator, respectively) at a temperature of about 25° C. with a mechanical mixer at about 350 RPM until solution is formed.

The aqueous phase is preferably prepared in a separate mixing system, dissolving sodium chloride ("NaCl") and 2-hydroxyethyl methacrylate ("HEMA") (stabilizer and hydrophilic monomer, respectively) in water until completely dissolved at a temperature of about 25° C.

The aqueous phase is preferably then added in small portions continuously (to prevent phase inversion) to the oil phase while mixing at about 450 RPM until the desired ratio is reached. After the aqueous phase is fully dispersed the emulsion is continued to mix at about 550 RPM for about 15 minutes for further droplet breakup to encourage droplet uniformity.

The emulsion is then cast into the desired mold that is preferably lined with a fabric backing either by pouring or injection, and thermally cured at about 70° C. for about four hours. The liner is then removed from the cast and dried at about 50° C. to remove the aqueous phase and initiate window formation that facilitate the interconnectivity.

The preceding example merely illustrates an exemplary embodiment, but desirable results can be achieved by substituting the specific times, temperatures and chemicals for other times, temperatures, and/or chemicals.

Note that in the specification and claims, "about" or "approximately" means within twenty percent (20%) of the numerical amount cited.

Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another.

What is claimed is:

1. A method for producing a material comprising:
producing interconnected pore spaces within a continuous phase of a hydrophobic polymer by employing internal phase emulsion templating, the internal phase emulsion templating selected from medium internal phase emulsion ("MIPE") templating and/or high internal phase emulsion ("HIPE") templating;
producing a hydrophilic pore lining from hydrophilic chemical end groups of a second polymer lined within the interconnected pore spaces of the hydrophobic polymer, the hydrophilic chemical end groups produced from a hydrophilic monomer polymerized selectively at a surface of the hydrophobic polymer, wherein an aqueous phase containing a hydrophilic monomer is dispersed into the continuous phase of the hydrophobic polymer prior to Polymerization of the hydrophobic polymer; and
crosslinking together the continuous phase of the hydrophobic polymer to the hydrophilic pore lining via covalent interaction using a chain crosslinker.

2. The method of claim 1 wherein the hydrophobic monomers, the chain crosslinker, and an additive are used in the continuous phase of the hydrophobic polymer.

3. The method of claim 1 wherein the internal phase emulsion templating is stabilized with one or more surfactants.

4. The method of claim 1 further comprising the hydrophilic monomer copolymerizing with the hydrophobic monomer at an aqueous-oil interface.

5. The method of claim 1 further comprising passing a mixture of the continuous phase and the aqueous phase through a barrier with a plurality of openings to cause the aqueous phase of the mixture to break up.

6. The method of claim 1 further comprising passing a mixture of the continuous phase and the aqueous phase through a static blade to cause the aqueous phase of the mixture to break up.

7. The method of claim 1 wherein connection of the interconnected pores occurs during a polymerization reaction and voids of the interconnected pores are subsequently emptied of any components that are occupying the voids of the interconnected pores after polymerization.

8. The method of claim 1 wherein employing internal phase emulsion templating comprises employing a hydrophilic, porous polyHIPE foam.

9. The method of claim 8 wherein employing a hydrophilic, porous polyHIPE foam comprises a foam with interconnected hydrophilic pores with a hydrophobic core.

10. The method of claim 1 wherein the step of employing internal phase emulsion templating comprises employing a hydrophilic, porous polyMIPE foam.

11. The method of claim 1 wherein employing a hydrophilic, porous polyMIPE foam comprises a foam with interconnected hydrophilic pores with a hydrophobic core.

12. The method of claim 1 further comprising producing hydrophilic chemical end groups from a material selected from the group consisting of: 2-hydroxyethyl acrylate, 2-hydroxyethyl methacrylate, sodium acrylate, 2-hydroxyethyl acrylate, poly(propylene fumarate), poly(propylene glycol)-acrylates and diacrylates, poly(propylene glycol)-methacrylates and dimethacrylates, poly(ethylene glycol)-acrylates and diacrylates, poly(ethylene glycol)-methacrylates and dimethacrylates, acrylic acid, N-isopropyl acrylamide, acrylamide, acrylonitrile, glacial methacrylic acid, 2-(acryloyloxy)ethyl-trimethylammonium chloride, [2-(methacryloyloxy)ethyl]trimethyl ammonium, N,N'Methylene(bis)acrylamide, N,N-diethylacrylamide, N,N-Diethylaminoethyl methacrylate, N,N-Diethylaminoethyl methacrylate, and 2-acrylamido-2-methyl-1-propanesulfonic acid, and a combination thereof.

13. The method of claim 1 further comprising pouring an emulsion into a gap between a mold and a cast and allowing the emulsion to cure therein.

14. The method of claim 1 further comprising shaping the material into a prosthetic liner.

15. The method of claim 1 further comprising shaping the material into a sleeve.

16. The method of claim 1 further comprising providing an additive to the continuous phase of the hydrophobic polymer prior to dispersal of the hydrophilic monomer to increase elasticity and/or strength of the material.

17. The method of claim 16 wherein providing the additive comprises providing a second material selected from the group consisting of silica micro-particles, silica nano-particles, clay particles, carbon nanotubes, nanocellulose, high molecular weight polymers, and a combination thereof.

18. The method of claim 1 further comprising adjusting a density of the produced material by adjusting a ratio of the dispersed aqueous phase with respect to the continuous phase.

* * * * *